United States Patent
Igarashi et al.

(10) Patent No.: US 10,456,022 B2
(45) Date of Patent: Oct. 29, 2019

(54) IMAGING DEVICE, ENDOSCOPE, AND ENDOSCOPE SYSTEM

(71) Applicant: OLYMPUS CORPORATION, Tokyo (JP)

(72) Inventors: Takatoshi Igarashi, Ina (JP); Noriyuki Fujimori, Suwa (JP); Makoto Ono, Sagamihara (JP); Masashi Saito, Akishima (JP); Satoru Adachi, Tsuchiura (JP); Nana Akahane, Yamanashi (JP); Takanori Tanaka, Hachioji (JP); Katsumi Hosogai, Tsukuba (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/939,740

(22) Filed: Mar. 29, 2018

(65) Prior Publication Data
US 2018/0220879 A1 Aug. 9, 2018

Related U.S. Application Data

(63) Continuation of application No. PCT/JP2016/078311, filed on Sep. 26, 2016.

(30) Foreign Application Priority Data

Oct. 1, 2015 (JP) .................. 2015-196254

(51) Int. Cl.
*A61B 1/05* (2006.01)
*H01L 25/065* (2006.01)
(Continued)

(52) U.S. Cl.
CPC ............ *A61B 1/05* (2013.01); *A61B 1/00195* (2013.01); *A61B 1/045* (2013.01); *A61B 1/063* (2013.01);
(Continued)

(58) Field of Classification Search
CPC ........................................................ A61B 1/05
See application file for complete search history.

(56) References Cited

U.S. PATENT DOCUMENTS 8,669,602 B2 * 3/2014 Hayashi .............. H01L 27/1461
257/292
9,018,628 B2 4/2015 Nagata
(Continued)

FOREIGN PATENT DOCUMENTS

JP H10-074790 A 3/1998
JP 2010-245506 A 10/2010
(Continued)

OTHER PUBLICATIONS

International Search Report dated Nov. 29, 2016 issued in PCT/JP2016/078311.
(Continued)

*Primary Examiner* — James M Pontius
(74) *Attorney, Agent, or Firm* — Scully, Scott, Murphy & Presser, P.C.

(57) ABSTRACT

An imaging device includes: a first chip including a light receiving unit, and a read circuit; a second chip including a timing control circuit, an A/D conversion circuit, and a cable transmission circuit; and a connection unit configured to connect the first and the second chips. The read circuit includes a column read circuit and a horizontal selection circuit, and a vertical selection circuit. The connection unit of the first chip is provided in a first area along a side of the rectangular light receiving unit, and in a second area adjacent to the column read circuit, the horizontal selection circuit, and the vertical selection circuit. The connection unit of the second chip is provided in a third area around the timing control circuit, the A/D conversion circuit, and the
(Continued)

cable transmission circuit and in a fourth area adjacent to the timing control circuit and the A/D conversion circuit.

11 Claims, 14 Drawing Sheets

(51) Int. Cl.
| | |
|---|---|
| *H01L 25/07* | (2006.01) |
| *H01L 25/16* | (2006.01) |
| *H01L 25/18* | (2006.01) |
| *H01L 27/14* | (2006.01) |
| *H01L 27/146* | (2006.01) |
| *H04N 5/378* | (2011.01) |
| *A61B 1/00* | (2006.01) |
| *A61B 1/045* | (2006.01) |
| *A61B 1/06* | (2006.01) |
| *H01L 21/66* | (2006.01) |
| *H04N 5/345* | (2011.01) |
| *H04N 5/376* | (2011.01) |
| *H04N 7/10* | (2006.01) |
| *H04N 5/225* | (2006.01) |
| *H04N 5/232* | (2006.01) |
| *H04N 5/369* | (2011.01) |

(52) U.S. Cl.
CPC ............ *A61B 1/0638* (2013.01); *H01L 22/32* (2013.01); *H01L 25/065* (2013.01); *H01L 25/07* (2013.01); *H01L 25/16* (2013.01); *H01L 25/18* (2013.01); *H01L 27/14* (2013.01); *H01L 27/146* (2013.01); *H01L 27/1469* (2013.01); *H01L 27/14618* (2013.01); *H01L 27/14634* (2013.01); *H01L 27/14636* (2013.01); *H04N 5/2256* (2013.01); *H04N 5/23203* (2013.01); *H04N 5/345* (2013.01); *H04N 5/378* (2013.01); *H04N 5/379* (2018.08); *H04N 5/3765* (2013.01); *H04N 7/102* (2013.01); *H04N 2005/2255* (2013.01)

(56) References Cited

U.S. PATENT DOCUMENTS

| | | | |
|---|---|---|---|
| 9,252,084 B2 | 2/2016 | Nagata | |
| 9,319,569 B2 | 4/2016 | Umebayashi et al. | |
| 9,530,812 B2 | 12/2016 | Umebayashi et al. | |
| 9,848,147 B2 | 12/2017 | Wakabayashi | |
| 2010/0238331 A1 | 9/2010 | Umebayashi et al. | |
| 2010/0245647 A1* | 9/2010 | Honda | H01L 27/14634 348/308 |
| 2012/0298993 A1 | 11/2012 | Nagata | |
| 2014/0232916 A1* | 8/2014 | Nagai | H03M 1/56 348/302 |
| 2014/0264847 A1 | 9/2014 | Takahashi | |
| 2014/0320618 A1 | 10/2014 | Akahane et al. | |
| 2015/0163403 A1 | 6/2015 | Wakabayashi | |
| 2017/0092681 A1 | 3/2017 | Umebayashi et al. | |
| 2018/0012924 A1 | 1/2018 | Umebayashi et al. | |
| 2018/0076243 A1* | 3/2018 | Tashiro | H01L 27/146 |
| 2018/0197902 A1* | 7/2018 | Nakamura | H01L 27/146 |
| 2018/0337209 A1* | 11/2018 | Narui | H01L 27/146 |
| 2019/0006412 A1* | 1/2019 | Ando | H01L 27/146 |

FOREIGN PATENT DOCUMENTS

| | | |
|---|---|---|
| JP | 2012-244100 A | 12/2012 |
| JP | 2014-017834 A | 1/2014 |
| JP | 2014-179433 A | 9/2014 |
| JP | 2015-153930 A | 8/2015 |
| WO | WO 2014/007004 A1 | 1/2014 |
| WO | WO 2014/115390 A1 | 7/2014 |
| WO | WO 2015/107948 A1 | 7/2015 |

OTHER PUBLICATIONS

JP Notification of Reason for Refusal dated Sep. 5, 2017 issued in JP 2017-541720.

* cited by examiner

IMAGING DEVICE, ENDOSCOPE, AND ENDOSCOPE SYSTEM

CROSS-REFERENCE TO RELATED APPLICATION

This application is a continuation of PCT International Application No. PCT/JP2016/078311 filed on Sep. 26, 2016 which claims the benefit of priority from Japanese Patent Application No. 2015-196254, filed on Oct. 1, 2015, the entire contents of which are incorporated herein by reference.

BACKGROUND

The present disclosure relates to an imaging device, an endoscope, and an endoscope system.

Imaging devices such as complementary metal-oxide semiconductors (CMOS) include a light receiving unit that has a plurality of pixels; and a peripheral circuit such as a read circuit that reads signals from the light receiving unit.

Furthermore, with endoscopes, there is a need to transmit imaging signals, captured at the distal end of an insertion unit that is inserted into a body cavity, to an image processing device via a cable. If imaging signals are transmitted as analog signals without change via a cable, a pixel rate is limited, and it is difficult to improve an image quality due to an increase in the number of pixels in an imaging device. Therefore, imaging devices for endoscopes need to include an A/D conversion circuit that conducts analog/digital (A/D) conversion on imaging signals.

Japanese Laid-open Patent Publication No. 2014-17834 discloses a column-parallel AD conversion circuit where a peripheral circuit is provided in a separate chip in order to reduce a chip area. With this configuration, a chip having a pixel area and a chip having a peripheral circuit are laminated, and the chips are connected with a through-silicon via (TSV: Si through-electrode), or the like.

SUMMARY

An imaging device according to one aspect of the present disclosure includes: a first chip including a light receiving unit including pixels arranged in a two-dimensional matrix and configured to generate and output an imaging signal that corresponds to a received amount of light, and a read circuit configured to sequentially select a predetermined pixel from the pixels and read the imaging signal output from the selected pixel; a second chip connected to a back side of a light incidence surface of the first chip by being laminated along a direction perpendicular to a surface where the pixels of the light receiving unit are arranged, the second chip including a timing control circuit configured to control a timing at which the read circuit reads the imaging signal output from the pixel selected, an A/D conversion circuit configured to conduct A/D conversion on an analog signal output from the first chip, and a cable transmission circuit configured to transmit a digital signal output from the A/D conversion circuit to a transmission cable; and a connection unit configured to electrically connect the first chip and the second chip, wherein the light receiving unit is rectangular, the read circuit includes a column read circuit and a horizontal selection circuit provided along one side of the rectangular light receiving unit, and a vertical selection circuit provided along one side of the rectangular light receiving unit perpendicular to the side along which the column read circuit and the horizontal selection circuit are arranged, the connection unit of the first chip is provided in a first area along a side of the rectangular light receiving unit along which the column read circuit, the horizontal selection circuit, and the vertical selection circuit are not provided, and in a second area that is adjacent to the column read circuit, the horizontal selection circuit, and the vertical selection circuit, the connection unit of the second chip is provided in a third area around the timing control circuit, the A/D conversion circuit, and the cable transmission circuit and in a fourth area that is adjacent to the timing control circuit and the A/D conversion circuit, and the first area and the third area are provided by being overlapped with each other and the second area and the fourth area are provided by being overlapped with each other in a direction perpendicular to the surface where the pixels of the light receiving unit are provided.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
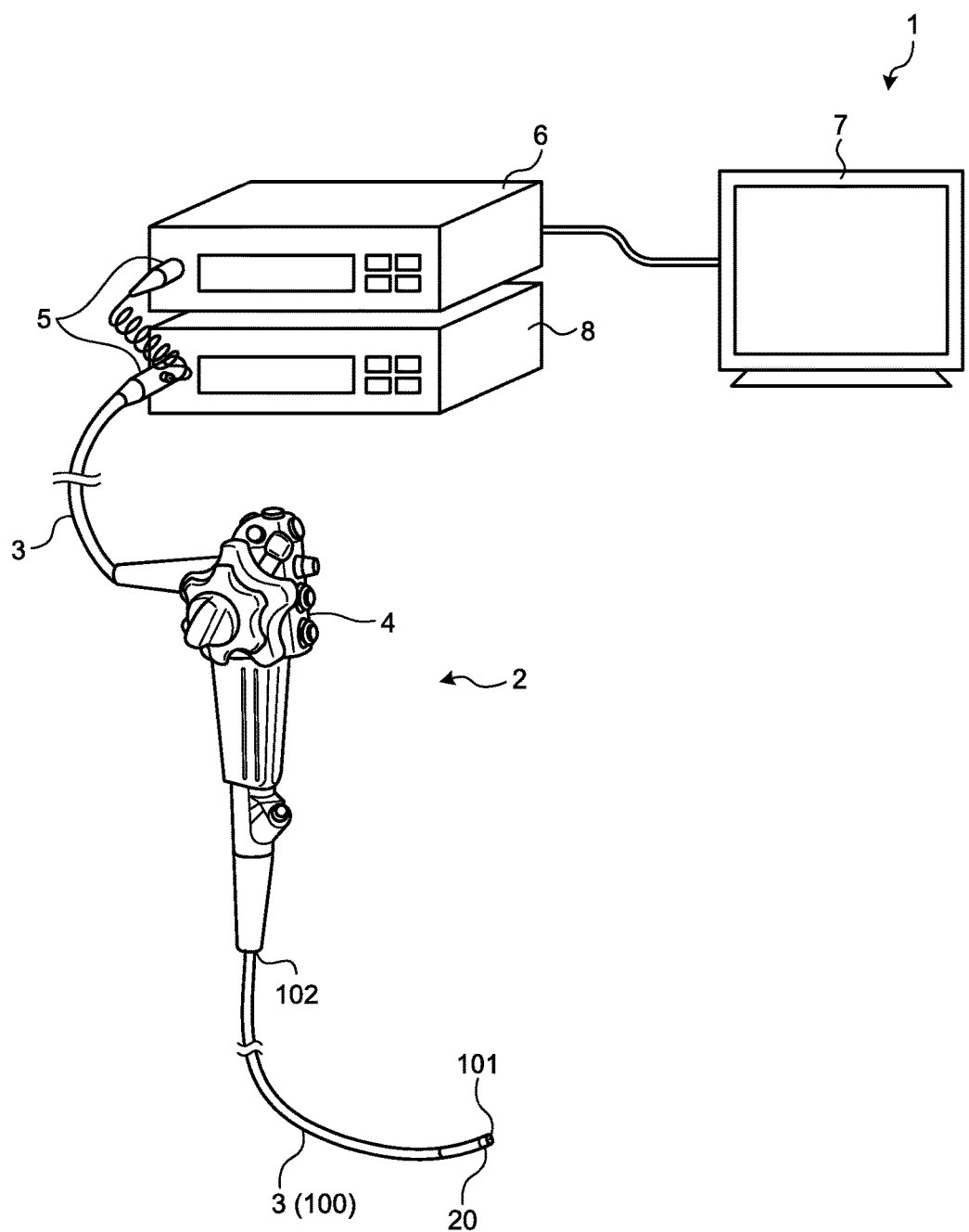
FIG. 1 is a schematic diagram that illustrates a configuration of the overall endoscope system that includes an imaging device according to a first embodiment.

As an embodiment for implementing the present disclosure, an explanation is given below of an endoscope system that includes an endoscope having its distal end inserted into a subject. Here, the present disclosure is not limited to the embodiment. Furthermore, in description of the drawings, the same elements are attached with the same reference numeral for explanation. Furthermore, it should be noted that the drawings are schematic and the relation between elements in thickness or width, the proportion of each element, and the like, are differ from reality. Moreover, each of the drawings includes parts where the dimension or proportion is different from each other.

First Embodiment

Configuration of the Endoscope System

FIG. 1 is a schematic diagram that illustrates a configuration of the overall endoscope system that includes an imaging device according to a first embodiment. An endoscope system 1 illustrated in FIG. 1 includes an endoscope 2, a transmission cable 3, an operating unit 4, a connector unit 5, a processor (processing device) 6, a display device 7, and a light source device 8.

The endoscope 2 includes an insertion unit 100 that may be inserted into the subject so that it inserts the insertion unit 100 into a body cavity of the subject to capture the inside of the body of the subject and then outputs imaging signals (image data) to the processor 6. Furthermore, in the endoscope 2, an imaging unit 20 (capturing device) that captures in-vivo images is provided at the side that is at one end of the transmission cable 3 and that is at a distal end 101 of the insertion unit 100 inserted into the body cavity of the subject, and the operating unit 4 that receives various operations for the endoscope 2 is provided at a proximal end 102 of the insertion unit 100. Imaging signals of images captured by the imaging unit 20 are output to the connector unit 5 via the transmission cable 3 having for example a length of several meters.

The transmission cable 3 connects the endoscope 2 and the connector unit 5 and also connects the endoscope 2 and the light source device 8. Furthermore, the transmission cable 3 propagates imaging signals generated by the imaging unit 20 to the connector unit 5. The transmission cable 3 is configured by using a cable, optical fiber, or the like.

The connector unit 5 is connected to the endoscope 2, the processor 6, and the light source device 8, and it transmits imaging signals output from the connected endoscope 2 to the processor 6.

The processor 6 conducts predetermined image processing on imaging signals input from the connector unit 5 and outputs them to the display device 7. Furthermore, the processor 6 controls the overall endoscope system 1 in an integrated manner. For example, the processor 6 performs control so as to switch the illumination light output from the light source device 8 or switch a capturing mode of the endoscope 2.

The display device 7 displays images that correspond to imaging signals on which the processor 6 has conducted image processing. Furthermore, the display device 7 displays various types of information regarding the endoscope system 1. The display device 7 is configured by using a display panel, or the like, which is a liquid crystal, organic electro luminescence (EL), or the like.

The light source device 8 emits illumination light toward the object from the side of the distal end 101 of the insertion unit 100 in the endoscope 2 via the connector unit 5 and the transmission cable 3. The light source device 8 is configured by using a white light emitting diode (LED) that emits white light, an LED that emits narrow band imaging (NBI) illumination light, which is narrow band light having a wavelength band that is narrower than that of white light, or the like. The light source device 8 emits white light or NBI illumination light toward the object via the endoscope 2 under the control of the processor 6. Furthermore, according to the first embodiment, the light source device 8 uses an illumination system with a simultaneous method.

Figure 2:
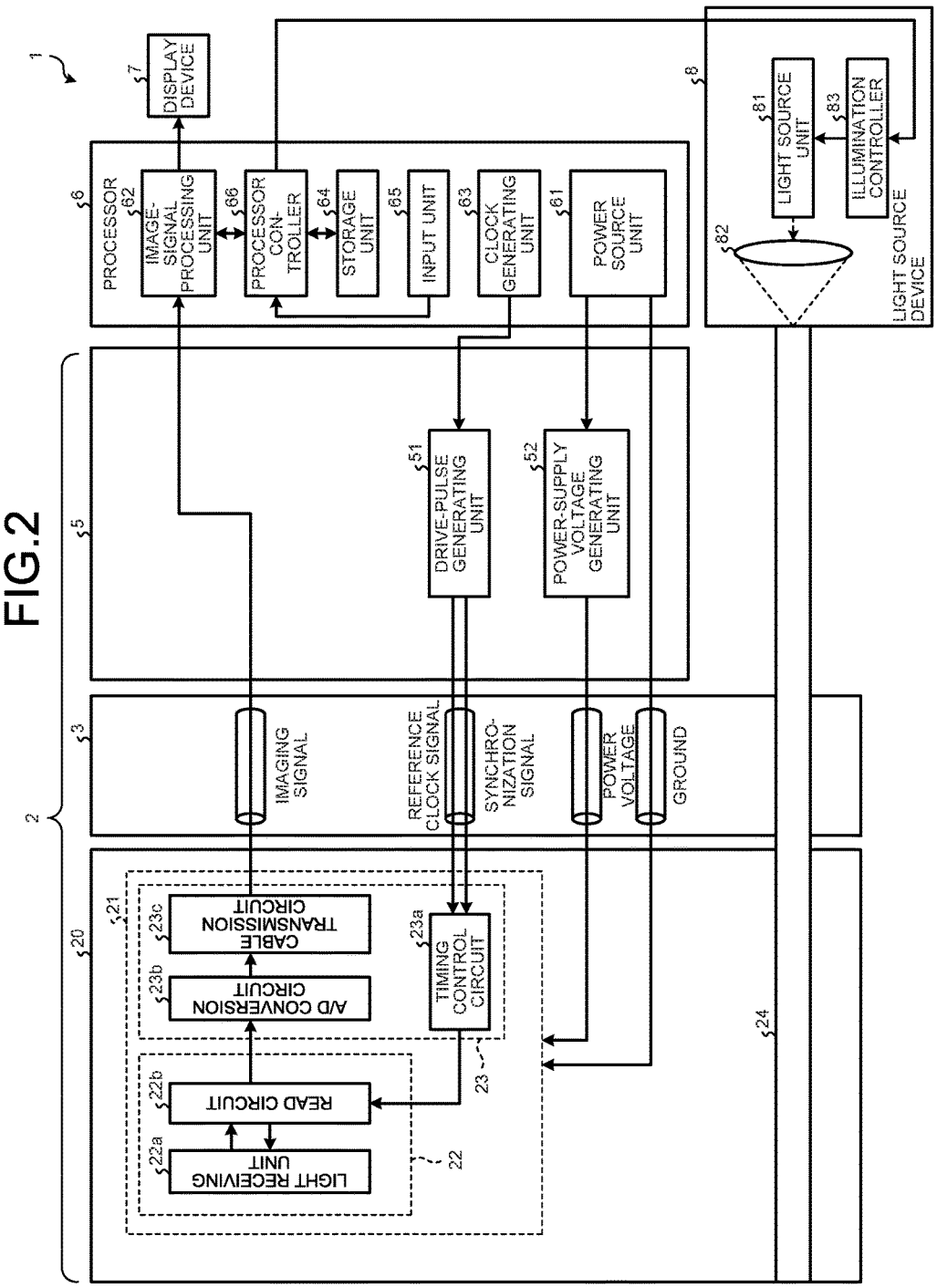
FIG. 2 is a block diagram that illustrates a function of the relevant part of the endoscope system that includes the imaging device according to the first embodiment.

FIG. 2 is a block diagram that illustrates a function of the relevant part of the endoscope system that includes the imaging device according to the first embodiment. With reference to FIG. 2, an explanation is given of the details of the configuration of each unit in the endoscope system 1 and the routes of electric signals in the endoscope system 1.

Configuration of the Endoscope

First, the configuration of the endoscope 2 is explained. The endoscope 2 illustrated in FIG. 2 includes the imaging unit 20, the transmission cable 3, and the connector unit 5.

The imaging unit 20 includes an imaging device 21. The imaging device 21 includes a CMOS image sensor (CIS) 22, which is a first chip, and an image signal processor (ISP) 23, which is a second chip, connected to each other in a laminated manner.

The CIS 22 includes a light receiving unit 22a that has pixels arranged in a two-dimensional matrix to generate and output imaging signals that correspond to the received amount of light; and a plurality of read circuits 22b that sequentially selects a predetermined pixel from the pixels in the light receiving unit 22a and reads an imaging signal output from the selected pixel, whereby it serves as a CIS.

The ISP 23 includes a timing control circuit 23a that controls the timing in which the read circuit 22b reads an imaging signal output from the selected pixel in the light receiving unit 22a; an A/D conversion circuit 23b that conducts A/D conversion on analog signals output from the CIS 22; and a cable transmission circuit 23c that transmits digital signals output from the A/D conversion circuit 23b to the transmission cable 3, whereby it serves as an ISP. Furthermore, more detailed explanation of the imaging device 21 is given later.

A light guide 24 emits illumination light output from the light source device 8 toward the object. The light guide 24 is implemented by using a glass fiber, illumination lens, or the like.

The connector unit 5 includes a drive-pulse generating unit 51 and a power-supply voltage generating unit 52.

The drive-pulse generating unit 51 generates a synchronization signal indicating the start position of each frame in accordance with a reference clock signal (e.g., a clock signal of 27 MHz), which is supplied from the processor 6 and is used as a reference for operation of each component in the endoscope 2, and outputs it together with the reference clock signal to the timing control circuit 23a of the imaging unit 20 via the transmission cable 3. Here, synchronization signals generated by the drive-pulse generating unit 51 include horizontal synchronization signals and vertical synchronization signals.

The power-supply voltage generating unit 52 generates a power-supply voltage needed to drive the imaging unit 20 from the power supplied by the processor 6 and outputs it to the imaging unit 20. The power-supply voltage generating unit 52 uses a regulator, or the like, to generate the power-supply voltage needed to drive the imaging unit 20.

Configuration of the Processor

Next, the configuration of the processor 6 is explained. The processor 6 is a control device that controls the overall endoscope system 1 in an integrated manner. The processor 6 includes a power source unit 61, an image-signal processing unit 62, a clock generating unit 63, a storage unit 64, an input unit 65, and a processor controller 66.

The power source unit 61 supplies the power to the power-supply voltage generating unit 52 and supplies the ground to the imaging unit 20 via the connector unit 5 and the transmission cable 3.

The image-signal processing unit 62 performs image processing, such as synchronization process, white balance (WB) adjustment process, gain adjustment process, gamma correction process, or format conversion process, on digital imaging signals that has undergone A/D conversion in the ISP 23 so as to convert them into image signals and then outputs the image signals to the display device 7.

The clock generating unit 63 generates a reference clock signal that is used as a reference for operation of each component in the endoscope system 1 and outputs the reference clock signal to the drive-pulse generating unit 51.

The storage unit 64 stores various types of information, data in processing, and the like, with regard to the endoscope system 1. The storage unit 64 is configured by using a recording medium such as a flash memory or a random access memory (RAM).

The input unit 65 receives input of various operations regarding the endoscope system 1. For example, the input unit 65 receives input of a command signal to switch the type of illumination light output from the light source device 8. The input unit 65 is configured by using, for example, a cross-shaped switch, a push button, or the like.

The processor controller 66 controls each unit included in the endoscope system 1 in an integrated manner. The processor controller 66 is configured by using a central processing unit (CPU), or the like. The processor controller 66 switches illumination light output from the light source device 8 in accordance with a command signal input from the input unit 65.

Configuration of the Light Source Device

Next, a configuration of the light source device 8 is explained. The light source device 8 includes a light source unit 81, a condenser lens 82, and an illumination controller 83.

The light source unit 81 outputs illumination light toward the light guide 24 via the condenser lens 82 under the control of the illumination controller 83. The light source unit 81 is configured by using a white LED. Although the light source unit 81 is configured by using a white LED according to the first embodiment, white light may be output by, for example, a xenon lamp or a red LED, a green LED, and a blue LED in combination. Furthermore, the endoscope system 1 may have an imaging function with NBI, auto fluorescence imaging (AFI), or infrared imaging (IRI).

The condenser lens 82 condenses illumination light output from the light source unit 81 and outputs it to the light guide 24. The condenser lens 82 is configured by using one or more lenses.

The illumination controller 83 controls the light source unit 81 under the control of the processor controller 66. Specifically, the illumination controller 83 causes the light source unit 81 to output the illumination light under the control of the processor controller 66. Furthermore, the illumination controller 83 controls the output timing in which the light source unit 81 outputs the illumination light.

Figure 3:
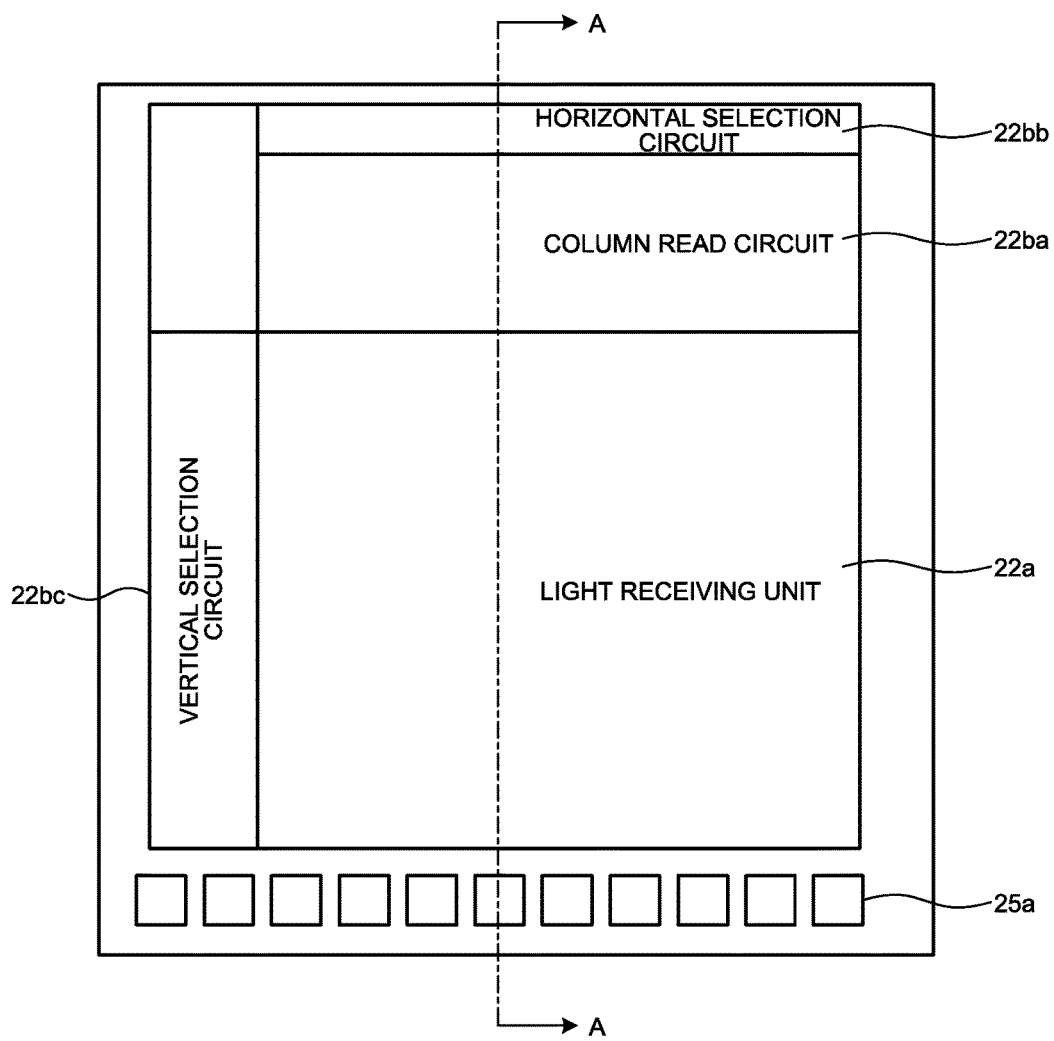
FIG. 3 is a top view of the imaging device according to the first embodiment.
Figure 4:
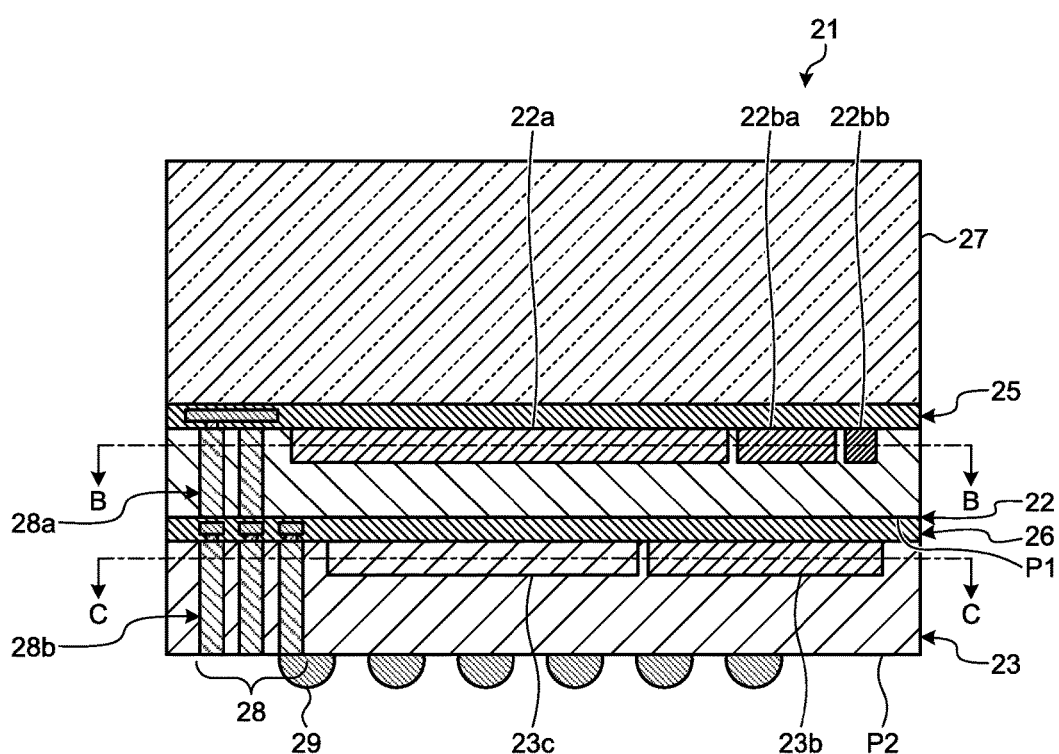
FIG. 4 is a cross-sectional view of the imaging device according to the first embodiment.
Figure 5:
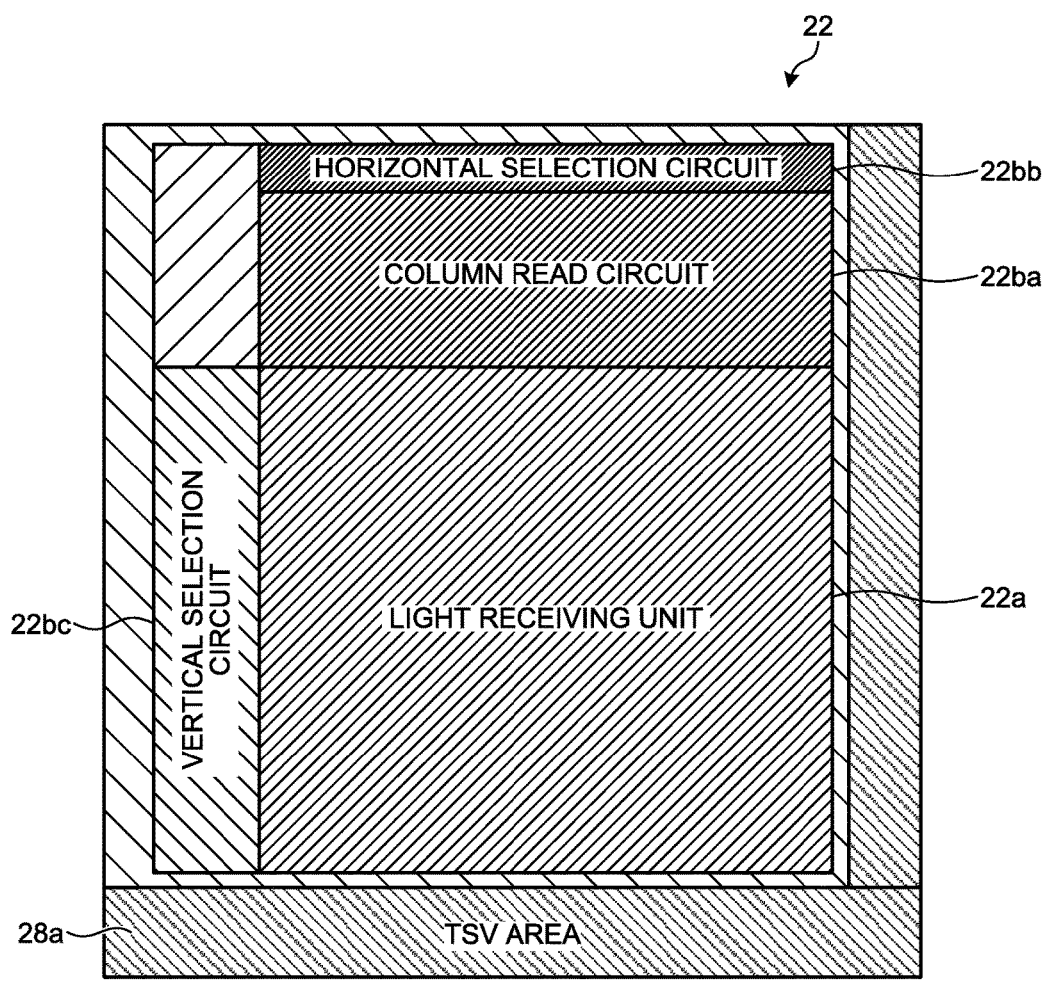
FIG. 5 is a cross-sectional view of a CIS in the imaging device according to the first embodiment.
Figure 6:
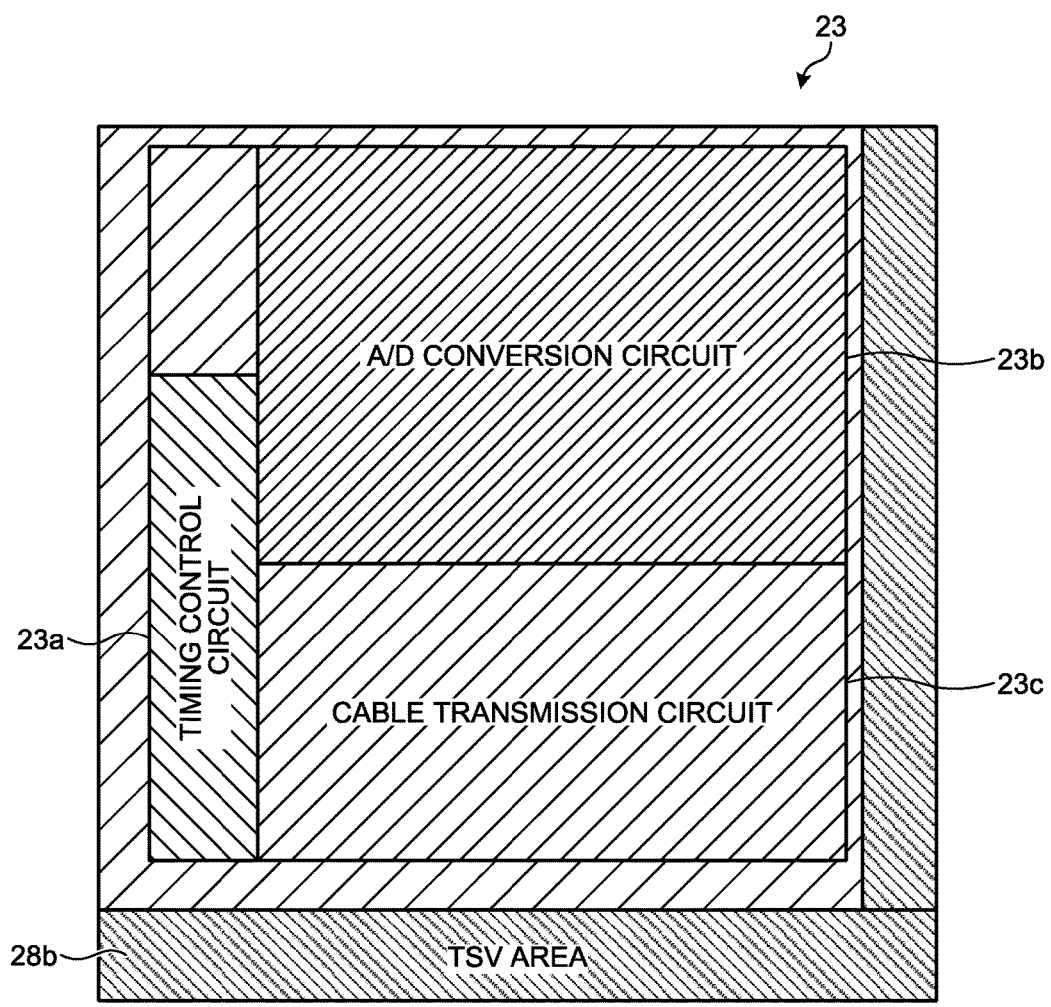
FIG. 6 is a cross-sectional view of an ISP in the imaging device according to the first embodiment.

Next, the imaging device 21 is explained in detail. FIG. 3 is a top view of the imaging device according to the first embodiment. FIG. 4 is a cross-sectional view of the imaging device according to the first embodiment. The cross-sectional view of FIG. 4 corresponds to the A-A line of FIG. 3. FIG. 5 is a cross-sectional view of the CIS in the imaging device according to the first embodiment. The cross-sectional view of FIG. 5 corresponds to the B-B line of FIG. 4. FIG. 6 is a cross-sectional view of the ISP in the imaging device according to the first embodiment. The cross-sectional view of FIG. 6 corresponds to the C-C line of FIG. 4.

As illustrated in FIG. 4, the imaging device 21 includes the CIS 22; the ISP 23 that is connected to the back side of the light incidence surface of the CIS 22 by being laminated along a direction (a vertical direction on the drawing plane of FIG. 4) perpendicular to the surface where the pixels of the light receiving unit 22a are arranged; a multi-laminate wiring layer 25 that is formed at the side of the light incidence surface of the CIS 22; a multi-laminate wiring layer 26 that is formed between the back side of the light incidence surface of the CIS 22 and the ISP 23; a cover glass 27; and a TSV 28 that electrically connects each layer. External terminals 29 are formed on the back side of the surface of the ISP 23 at the side of the CIS 22 by being formed through an undepicted rewiring layer to transmit and receive power and signals to and from an external unit. The external terminal 29 is connected to an undepicted board and is further connected to the transmission cable 3.

The TSV 28 includes a TSV 28a that is a first Si through-electrode that passes through the CIS 22; and a TSV 28b that is a second Si through-electrode that passes through the ISP 23. The CIS 22 and the ISP 23 are electrically connected with the TSV 28a. The ISP 23 and the external terminal 29 are electrically connected with the TSV 28b.

As illustrated in FIGS. 3 and 5, the light receiving unit 22a of the CIS 22 is rectangular. The read circuit 22b includes a column read circuit 22ba, a horizontal selection circuit 22bb, and a vertical selection circuit 22bc, and it reads an imaging signal from each pixel of the light receiving unit 22a. The column read circuit 22ba and the horizontal selection circuit 22bb are arranged along one side of the rectangular light receiving unit 22a. The vertical selection circuit 22bc is arranged along one side perpendicular to the side of the rectangular light receiving unit 22a along which the column read circuit 22ba and the horizontal selection circuit 22bb are arranged.

FIGS. 5 and 6 illustrate an area (TSV area) where the TSV 28a or the TSV 28b is formed. The TSV area (the TSV 28a) functions as a connection unit that electrically connects the CIS 22 and the ISP 23. The TSV 28a is provided at an area along a side of the rectangular light receiving unit 22a along which the column read circuit 22ba, the horizontal selection circuit 22bb, or the vertical selection circuit 22bc *is not arranged*.

As illustrated in FIG. 6, in the ISP 23, the TSV 28b is provided at an area around the area where the timing control circuit 23a, the A/D conversion circuit 23b, and the cable transmission circuit 23c are arranged.

Figure 7:
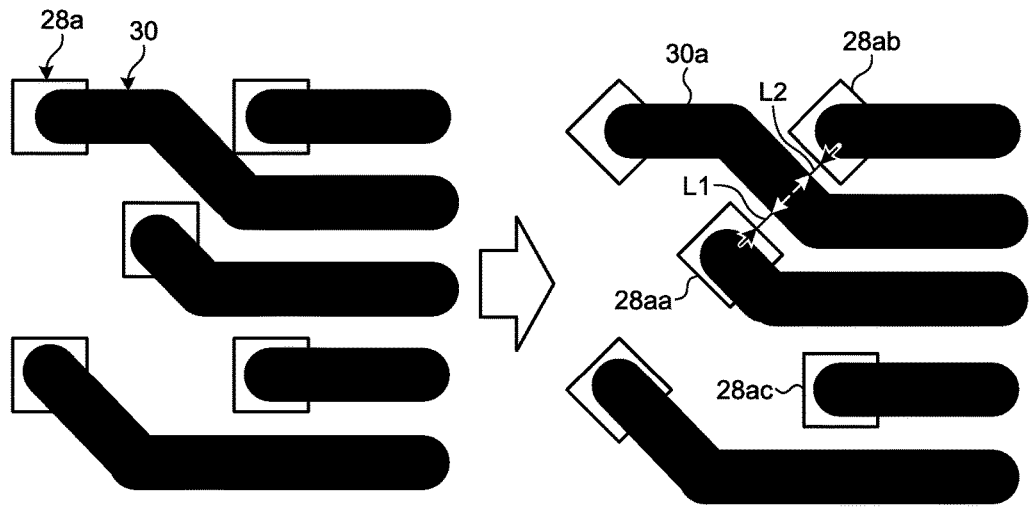
FIG. 7 is a partially enlarged view when the CIS of FIG. 4 is viewed from the back side of the light incidence surface.

FIG. 7 is a partially enlarged view when the CIS of FIG. 4 is viewed from the back side of the light incidence surface. As illustrated in FIG. 7, on the back side (a side P1 in FIG. 4) of the light incidence surface of the CIS 22, a rewiring layer having a plurality of lead wires 30 is formed. Each electrode of the TSV 28a has a rectangle cross section and is arranged in a grid pattern.

It is preferable that the TSV 28a is provided such that it is located away from the lead wires 30 other than the connected lead wire 30. Therefore, in the rewiring layer, each electrode of the TSV 28a is provided such that one side of the rectangle of each of the TSVs 28a is parallel to the lead wire 30 that passes by two sides of the TSV 28a. For example, in the right section of FIG. 7, a TSV 28aa and a TSV 28ab are rotated by 45 degrees from the positions in the left section of FIG. 7 so that they are provided such that one side of the rectangle, the TSV 28aa and the TSV 28ab, is parallel to a lead wire 30a. Accordingly, a distance L1 between the lead wire 30a and the TSV 28aa and a distance L2 between the lead wire 30a and the TSV 28ab may be larger. Conversely, a TSV 28ac is not rotated from the position in the left section of FIG. 7 so that the distance between the TSV 28ac and the lead wire 30 above or below the TSV 28ac may be larger.

In the same manner, on the back side (a side P2 in FIG. 4) of the surface of the ISP 23 at the side of the CIS 22, a rewiring layer having a plurality of lead wires is formed. Each electrode of the TSV 28b has a rectangle cross section and is arranged in a grid pattern. It is preferable that the TSV 28b is provided such that it is located away from the lead wires other than the connected lead wire. Therefore, in the rewiring layer, each electrode of the TSV 28b is provided such that one side of the rectangle of each of the TSVs 28b is parallel to the lead wire that passes by two sides of the TSV 28b.

Figure 8:
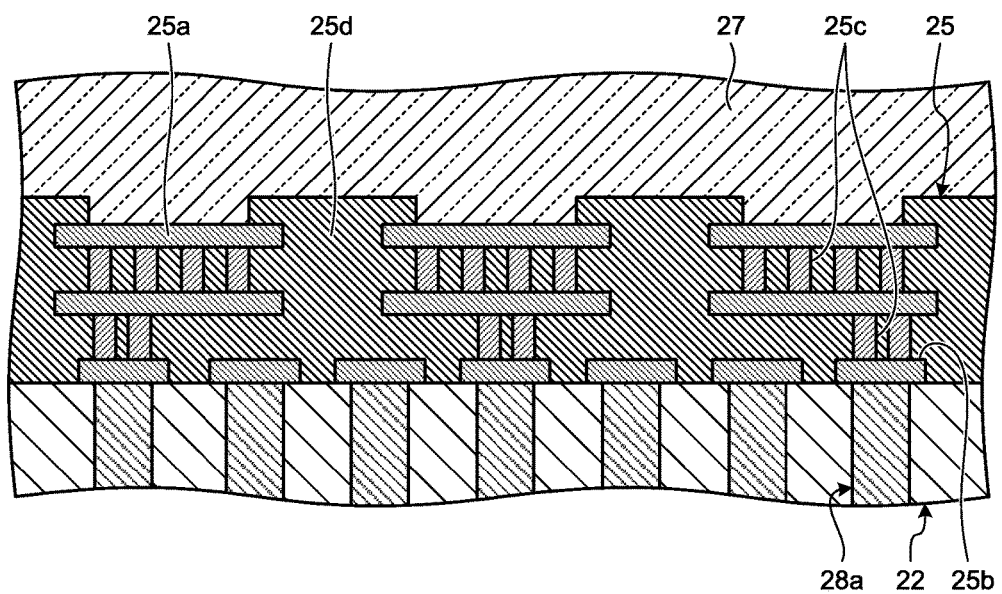
FIG. 8 is a partial cross-sectional view of the multi-laminate wiring layer of FIG. 4 in an enlarged manner.

FIG. 8 is a partial cross-sectional view of the multi-laminate wiring layer of FIG. 4 in an enlarged manner. As illustrated in FIG. 8, the multi-laminate wiring layer 25 has for example three wiring layers. In a layer of the multi-laminate wiring layer 25 at the side (the upper side in FIG. 8) of the light incidence surface, a probing pad 25a is formed so that it is brought into contact with a testing probe for conducting imaging test. In a layer of the multi-laminate wiring layer 25 at the side (the lower side in FIG. 8) of the CIS 22, a TSV connection pad 25b is formed as a connection pad for electrically connecting the multi-laminate wiring layer 25 and the TSV 28a. Contact plugs 25c electrically connect layers between the probing pad 25a and the TSV connection pad 25b. Furthermore, an interlayer insulating film 25d insulates the contact plugs 25c. In the multi-laminate wiring layer 25, the probing pads 25a are formed for wires that are needed for testing on VDD, VSS, or OUT, for example, so that imaging test may be conducted on the front side of the imaging device 21 before the cover glass 27 is formed.

Furthermore, a configuration may be such that, among the TSVs 28a that electrically connect the CIS 22 and the ISP 23, only the TSV 28a used for imaging test is electrically connected to the probing pad 25a via the TSV connection pad 25b. With this configuration, the number of the probing pads 25a, for which a large area is necessary for probing, may be kept to the minimum, and an increase in a chip area may be prevented.

Here, in the imaging device 21, the A/D conversion circuit 23b and the cable transmission circuit 23c, for which areas are required, are provided in the ISP 23 separately from the light receiving unit 22a, whereby a chip area may be smaller. Furthermore, in the imaging device 21, as the A/D conversion circuit 23b enables transmission of imaging signals as digital signals, high bandwidth transmission is enabled, and an increase in the number of pixels in the imaging device and an improvement in electric-cautery tolerance may be achieved. Furthermore, in the imaging device 21, the column read circuit 22ba (analog CDS circuit) suitable for size reduction is provided on the CIS 22. Furthermore, imaging signals are serially transmitted from the CIS 22 to the ISP 23 so that the CIS 22 and the ISP 23 may be connected with a small number of the TSVs 28, whereby a chip area occupied by the TSV 28 may be smaller. Accordingly, the imaging device 21 is an imaging device that has an A/D conversion function and that has a sufficiently small chip area.

Furthermore, in the imaging device 21, the TSV 28 is provided on the surrounding area illustrated in FIG. 5 or 6 so that the center of the imaging device 21 may substantially match the center of the light receiving unit 22a, whereby the size of the imaging unit 20 including the optical system may be reduced.

Figure 9:
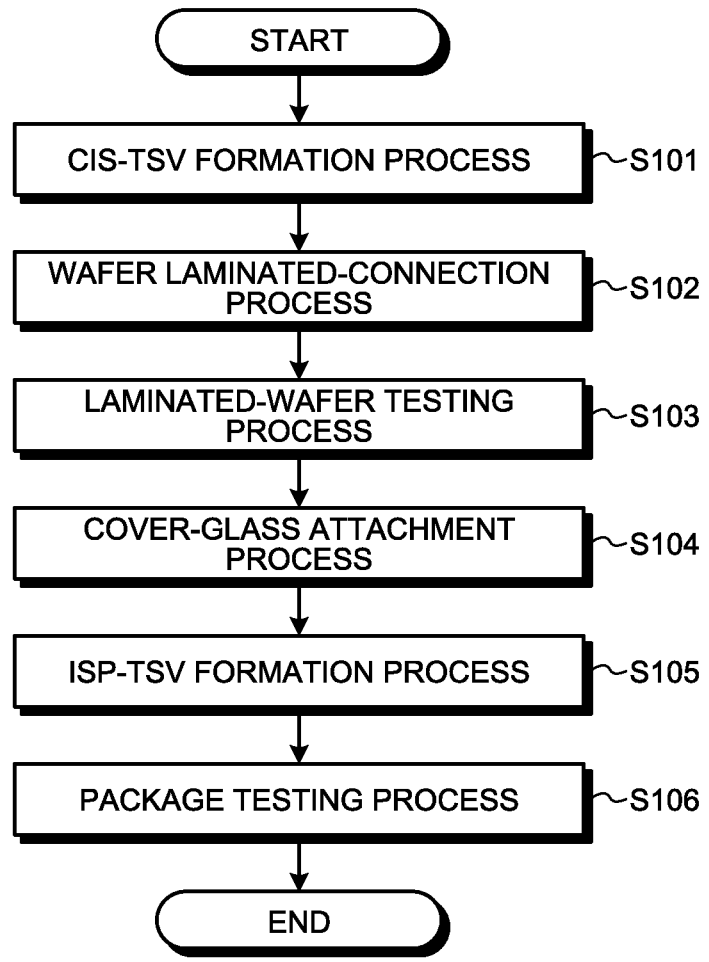
FIG. 9 is a flowchart that illustrates the outline of the method for manufacturing the imaging device according to the first embodiment.

Next, the method for manufacturing the imaging device 21 is explained. FIG. 9 is a flowchart that illustrates the outline of the method for manufacturing the imaging device according to the first embodiment. First, the CIS 22 and the ISP 23 are formed during a known semiconductor integrated circuit formation process.

Then, the TSV 28a is formed in the CIS 22 by using a known silicon etching process, deposition or photolithography process (Step S101). Furthermore, before or after the TSV 28a is formed in the CIS 22, the back side of the light incidence surface of the CIS 22 is removed as needed so that the CIS 22 is made thin to have a predetermined thickness. Here, it is preferable that, before the CIS 22 is made thin, a supporting board is temporarily attached to the light incidence surface side of the CIS 22 so that the CIS 22 may be easily handled after being made thin.

Then, two wafers, the CIS 22 and the ISP 23, are laminated, and they are mechanically and electrically connected (Step S102).

Here, a testing probe is brought into contact with the probing pad 25a on the front surface side of the CIS 22, and imaging test is conducted for the CIS 22 and the ISP 23 that are connected in a laminated manner (Step S103). Furthermore, if a supporting board is temporarily attached to the CIS 22, the supporting board is removed before imaging test so that the probing pad 25a is exposed, and then imaging test is conducted.

Then, the cover glass 27 is attached to the front surface of the CIS 22 through a transparent adhesion layer (Step S104).

Then, the TSV 28b is formed in the ISP 23 by using a known silicon etching process, deposition or photolithography process (Step S105). Furthermore, before or after the TSV 28b is formed in the ISP 23, the back side of the surface of the ISP 23 at the side of the CIS 22 is removed as needed so that the ISP 23 is made thin to have a predetermined thickness. Here, when the ISP 23 is made thin, no separate supporting board needs to be temporarily attached as the cover glass 27 attached at Step S104 is substituted for a supporting board. Furthermore, a rewiring layer and the external terminal 29 are formed on the back side of the surface of the ISP 23 at the side of the CIS 22.

Here, a testing probe is brought into contact with the external terminal 29 so that imaging test after package is conducted (Step S106). According to the steps described above, the imaging device 21 may be manufactured while imaging test is conducted.

MODIFIED EXAMPLE 1

Figure 10:
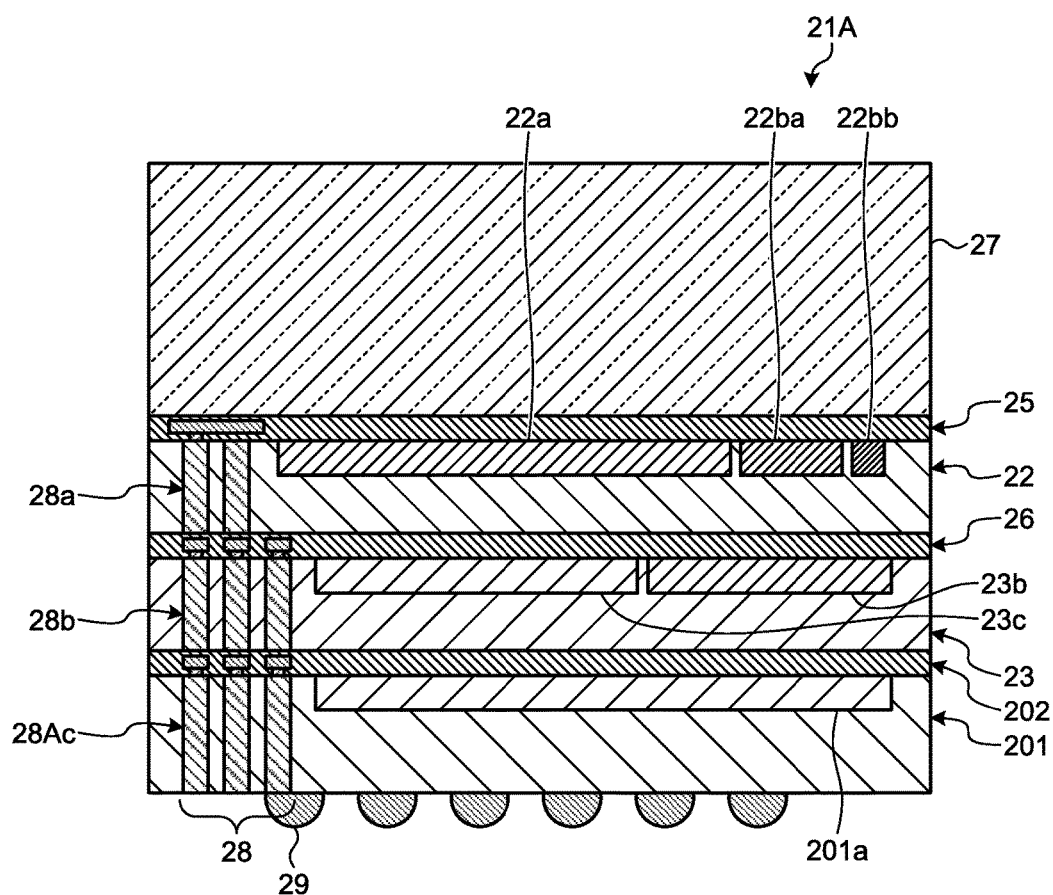
FIG. 10 is a cross-sectional view of an imaging device according to a modified example 1 of the first embodiment.

FIG. 10 is a cross-sectional view of an imaging device according to a modified example 1 of the first embodiment. As illustrated in FIG. 10, an imaging device 21A according to the modified example 1 includes a capacitor chip 201 further including a capacitor 201a on the back side of the surface of the ISP 23 at the side of the CIS 22; and a multi-laminate wiring layer 202 that is formed between the back side of the surface of the ISP 23 at the side of the CIS 22 and the capacitor chip 201. The capacitor 201a functions as a power-supply bypass capacitor. The ISP 23 and the capacitor chip 201 are electrically connected with the TSV 28b that passes through the ISP 23. The capacitor chip 201 and the external terminal 29 are electrically connected with a TSV 28Ac that passes through the capacitor chip 201. As in the modified example 1, the imaging device may be configured to further include many semiconductor layers as well as the two layers, the CIS and the ISP.

MODIFIED EXAMPLE 2

Figure 11:
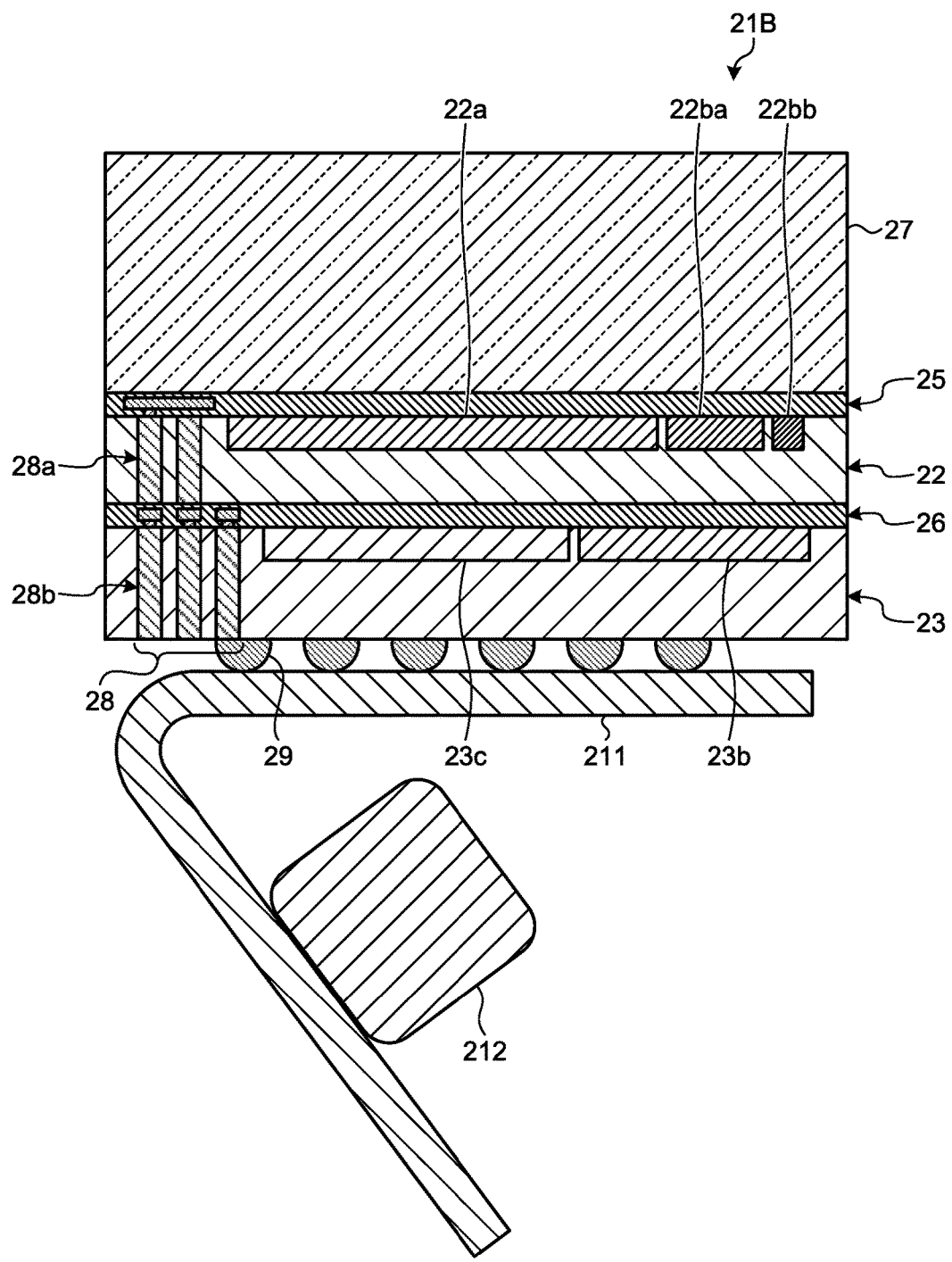
FIG. 11 is a cross-sectional view of an imaging device according to a modified example 2 of the first embodiment.

FIG. 11 is a cross-sectional view of an imaging device according to a modified example 2 of the first embodiment. As illustrated in FIG. 11, in an imaging device 21B according to the modified example 2, a flexible board 211 is connected to the external terminal 29, and a capacitor 212, which is a chip capacitor, is further provided on the flexible board 211. As in the modified example 2, a flexible board may be connected to an external terminal.

MODIFIED EXAMPLE 3

Figure 12:
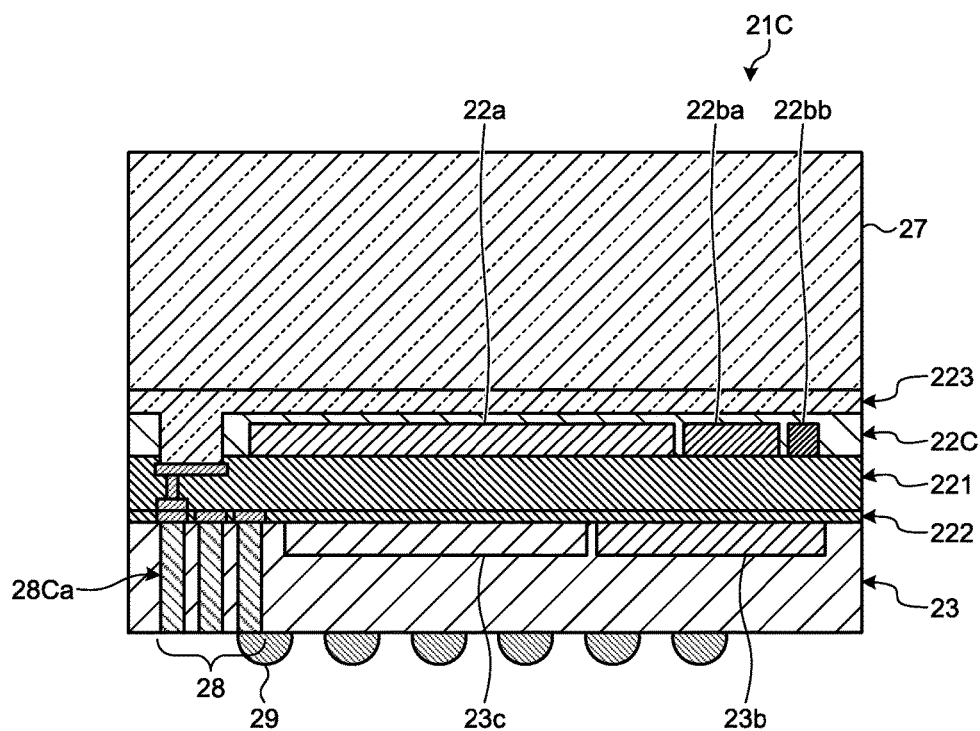
FIG. 12 is a cross-sectional view of an imaging device according to a modified example 3 of the first embodiment.

FIG. 12 is a cross-sectional view of an imaging device according to a modified example 3 of the first embodiment. As illustrated in FIG. 12, an imaging device 21C according to the modified example 3 includes a CIS-side multi-laminate wiring layer 221 and an ISP-side multi-laminate wiring layer 222 that electrically connect a CIS 22C and the ISP 23; and a transparent adhesive agent 223 that is attached between the CIS 22C and the cover glass 27. That is, in the imaging device 21C, no TSV passing through the CIS 22C is formed. The CIS 22C is a backside illumination (BSI) type imager chip, and power and signals are transmitted and received between the CIS 22C and the ISP 23 through a surface electrode of the CIS 22C. The ISP 23 and the external terminal 29 are electrically connected with a TSV 28Ca that passes through the ISP 23. As in the modified example 3, a connection unit that electrically connects the CIS and the ISP is not limited to TSV.

Figure 13:
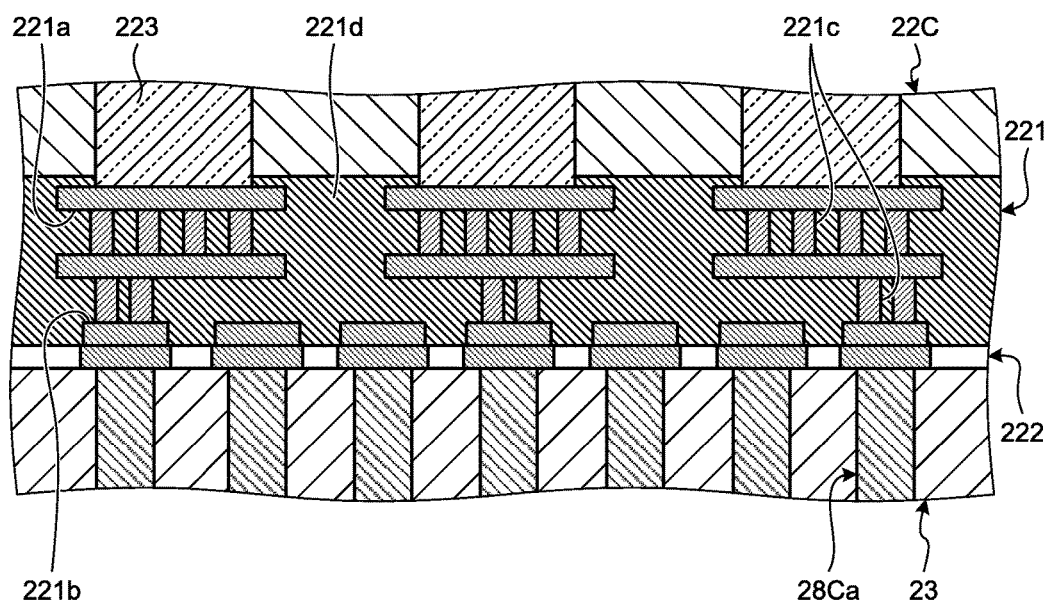
FIG. 13 is a partial cross-sectional view of the multi-laminate wiring layer of FIG. 12 in an enlarged manner.

FIG. 13 is a partial cross-sectional view of the multi-laminate wiring layer of FIG. 12 in an enlarged manner. As illustrated in FIG. 13, the CIS-side multi-laminate wiring layer 221, which is a multi-laminate wiring layer formed on the back side of the light incidence surface of the CIS 22C, has for example three wiring layers. A probing pad 221a is formed in a layer of the CIS-side multi-laminate wiring layer 221 at the side (upper side in FIG. 13) of the CIS 22C. A TSV connection pad 221b is formed in a layer of the CIS-side multi-laminate wiring layer 221 at the side (lower side in FIG. 13) of the ISP 23 as a connection pad that electrically connects the CIS-side multi-laminate wiring layer 221 and the TSV 28Ca. Contact plugs 221c electrically connect layers between the probing pad 221a and the TSV connection pad 221b. Furthermore, the interval between the contact plugs 221c is insulated by an interlayer insulating film 221d.

Furthermore, a configuration may be such that, among the signal lines (the contact plugs 221c) that electrically connect the CIS 22C and the ISP 23, only the signal line used for imaging test is electrically connected to the probing pad 221a via the TSV connection pad 221b. With this configuration, the number of the probing pads 221a, for which a large area is necessary for probing, may be kept to the minimum, and an increase in a chip area may be prevented.

Second Embodiment

Figure 14:
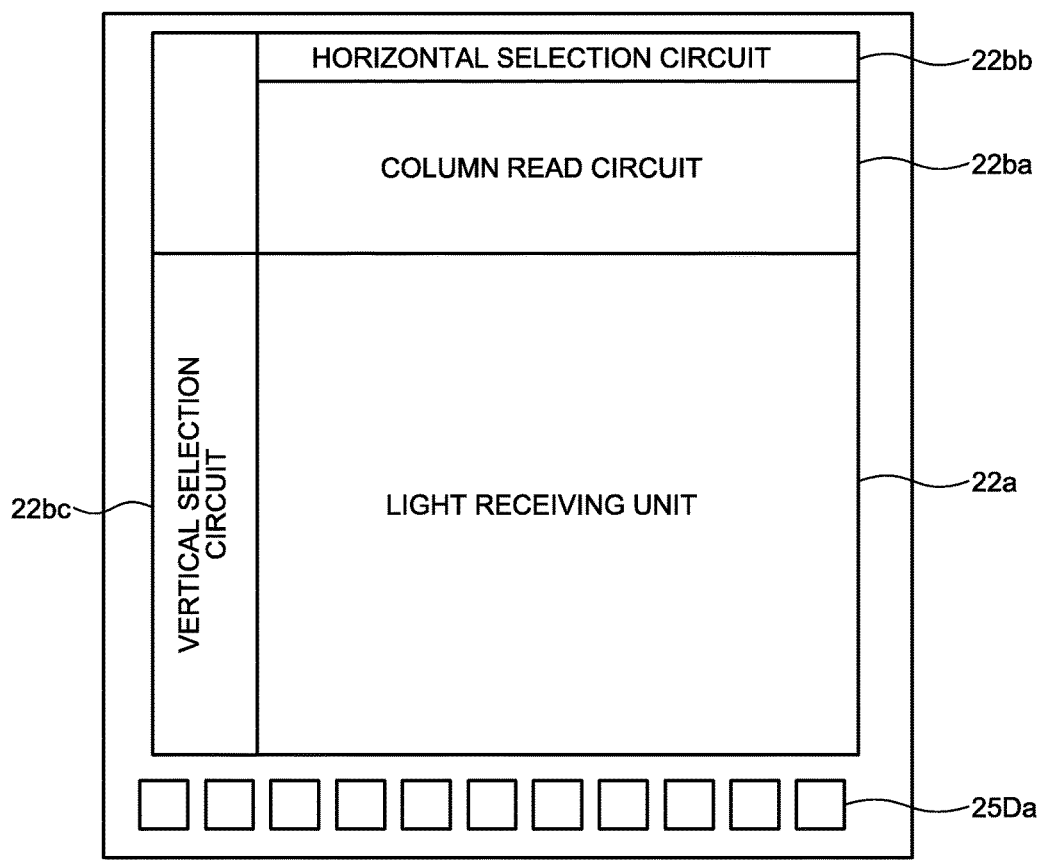
FIG. 14 is a top view of an imaging device according to a second embodiment.
Figure 15:
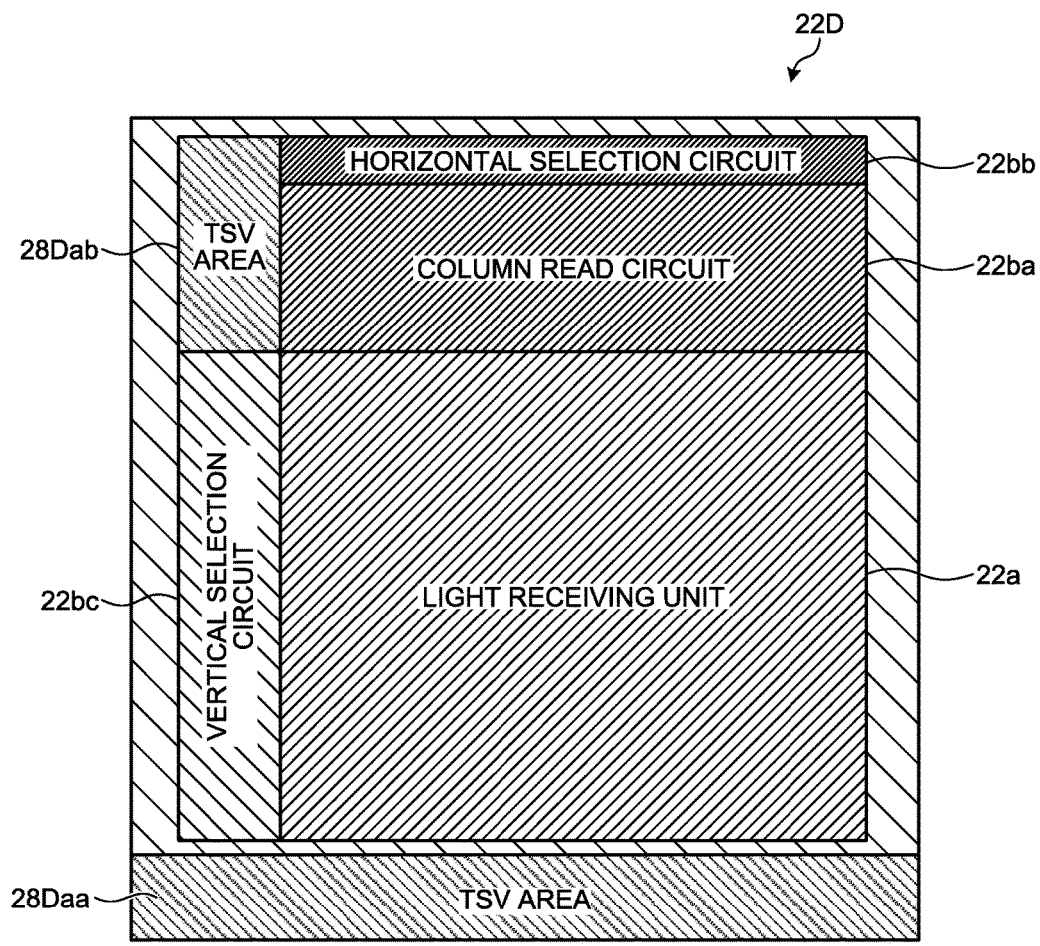
FIG. 15 is a cross-sectional view of a CIS of the imaging device according to the second embodiment.
Figure 16:
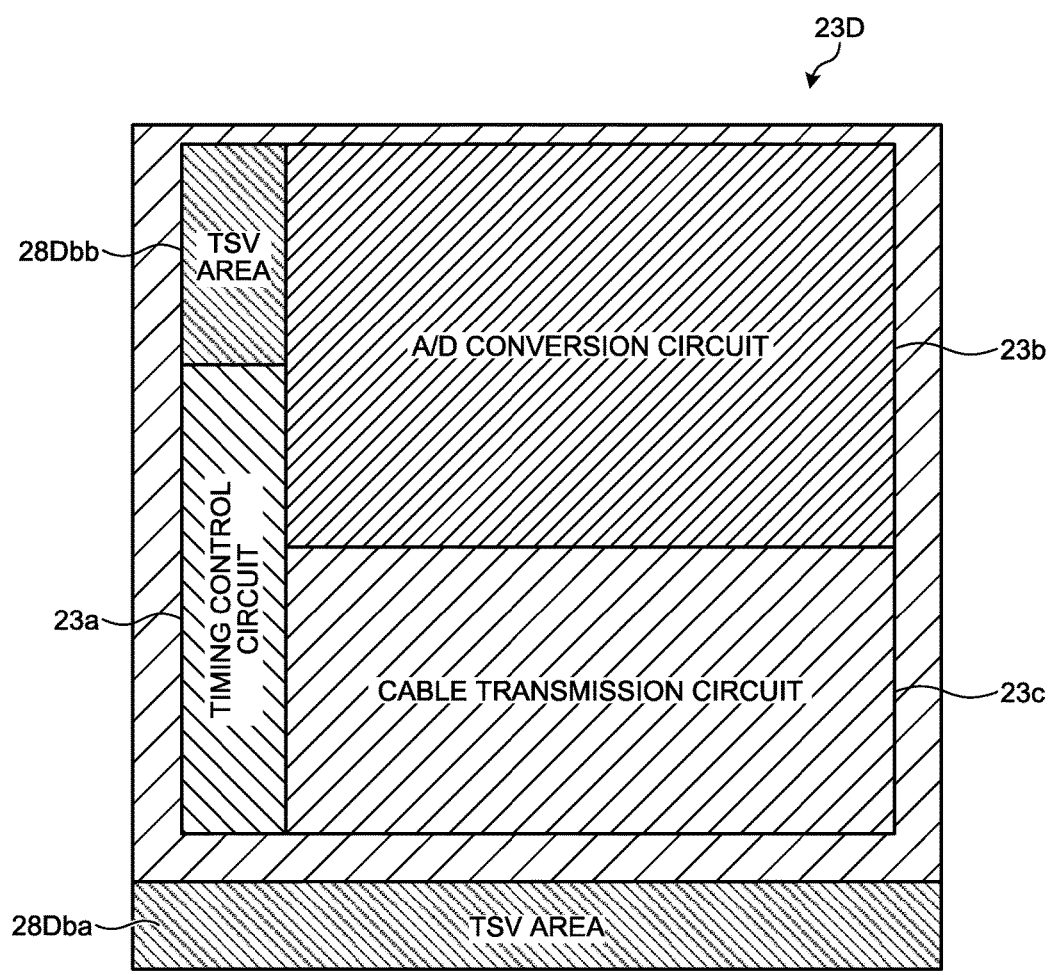
FIG. 16 is a cross-sectional view of an ISP of the imaging device according to the second embodiment.

FIG. 14 is a top view of an imaging device according to the second embodiment. FIG. 15 is a cross-sectional view of a CIS of the imaging device according to the second embodiment. FIG. 16 is a cross-sectional view of an ISP of the imaging device according to the second embodiment. As illustrated in FIGS. 14 to 16, as the imaging device of the second embodiment is different from that of the first embodiment in only arrangement of TSVs 28Daa, 28Dab, 28Dba, and a TSV 28Dbb and other configurations are the same as those in the first embodiment, explanation is omitted as appropriate.

As illustrated in FIG. 15, in a CIS 22D, the TSV 28Daa is provided at an area along one side at the opposing side of the side along which the column read circuit 22ba and the horizontal selection circuit 22bb are provided. Furthermore, in the CIS 22D, the TSV 28Dab is provided at an area surrounded by the column read circuit 22ba, the horizontal selection circuit 22bb, and the vertical selection circuit 22bc.

As illustrated in FIG. 16, in an ISP 23D, the TSV 28Dba and the TSV 28Dbb are provided at areas around the areas where the timing control circuit 23a, the A/D conversion circuit 23b, and the cable transmission circuit 23c are arranged.

As illustrated in FIGS. 15 and 16, in the imaging device according to the second embodiment, the TSV 28Daa, 28Dab, 28Dba, and the TSV 28Dbb are provided on spare spaces of the CIS 22D and the ISP 23D, whereby a chip area may be made efficiently small. As in the second embodiment, there is no particular limitation on arrangement of the TSV as long as the arrangement makes a chip area small.

According to the present disclosure, it is possible to implement an imaging device, an endoscope, and an endoscope system with an A/D conversion function and a sufficiently small chip area.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
   a first chip comprising:
      pixels arranged in a two-dimensional matrix and configured to generate and output an imaging signal that corresponds to a received amount of light; and
      a read circuit configured to sequentially select a predetermined pixel from the pixels and read the imaging signal output from the selected pixel;
   a second chip connected to a back side of a light incidence surface of the first chip by being laminated along a direction perpendicular to a surface where the pixels are arranged, the second chip comprising:
      a timing control circuit configured to control a timing at which the read circuit reads the imaging signal output from the pixel selected;
      an A/D conversion circuit configured to conduct A/D conversion on an analog signal output from the first chip; and
      a cable transmission circuit configured to transmit a digital signal output from the A/D conversion circuit to a transmission cable; and
   a connector configured to electrically connect the first chip and the second chip,
   wherein the two-dimensional matrix is rectangular,
   wherein the read circuit comprises:
      a column read circuit and a horizontal selection circuit provided along one side of the rectangular two-dimensional matrix; and
      a vertical selection circuit provided along one side of the rectangular two-dimensional matrix perpendicular to the one side along which the column read circuit and the horizontal selection circuit are provided, wherein the connector is provided in a first area along one side of the rectangular two-dimensional matrix along which the column read circuit, the horizontal selection circuit, and the vertical selection circuit are not provided, and in a second area that is adjacent to the column read circuit, the horizontal selection circuit, and the vertical selection circuit, wherein the connector is provided in a third area around the timing control circuit, the A/D conversion circuit, and the cable transmission circuit and in a fourth area that is adjacent to the timing control circuit and the A/D conversion circuit, and wherein the first area and the third area are provided by being overlapped with each other and the second area and the fourth area are provided by being overlapped with each other in a direction perpendicular to the surface where the pixels are provided.

2. The imaging device according to claim 1, wherein the first chip and the second chip are electrically connected with a plurality of first Si through-electrodes that pass through the first chip.

3. The imaging device according to claim 2, further comprising a multi-laminate wiring layer formed near the light incidence surface of the first chip, wherein a probing pad is formed in a layer of the multi-laminate wiring layer near the light incidence surface, and is configured to contact a testing probe for conducting imaging test, and wherein a connection pad is formed in a layer of the multi-laminate wiring layer near the first chip, the connection pad electrically connecting the multi-laminate wiring layer and the first Si through-electrode.

4. The imaging device according to claim 3, wherein among the first Si through-electrodes, only the first Si through-electrode used for imaging test is electrically connected to the probing pad via the connection pad.

5. The imaging device according to claim 2, wherein a rewiring layer including a plurality of lead wires is formed on a back side of the light incidence surface of the first chip, and wherein each of the first Si through-electrodes has a rectangle cross section and is arranged in a grid pattern, and is provided such that one side of the rectangle of the first Si through-electrode is parallel to the lead wire that passes by two sides of the first Si through-electrode in the rewiring layer.

6. The imaging device according to claim 5, wherein each of the first Si through-electrodes is provided such that each side of the rectangle intersects with an extending direction of the lead wires at 45 degrees.

7. The imaging device according to claim 1, further comprising an external terminal formed through rewiring on a back side of a surface of the second chip near the first chip and configured to transmit and receive power and a signal to and from an external unit, wherein the second chip and the external terminal are electrically connected with a second Si through-electrode that passes through the second chip.

8. The imaging device according to claim 7, further comprising a multi-laminate wiring layer formed on a back side of the light incidence surface of the first chip, wherein a probing pad is formed in a layer of the multi-laminate wiring layer near the first chip, and is configured to contact a testing probe for conducting imaging test, and wherein a connection pad is formed in a layer of the multi-laminate wiring layer at a side of the second chip, the connection pad electrically connecting the multi-laminate wiring layer and the second Si through-electrode.

9. The imaging device according to claim 7, wherein a rewiring layer comprising a plurality of lead wires is formed on a back side of a surface of the second chip near the first chip, and wherein each of the second Si through-electrode has a rectangle cross section and is arranged in a grid pattern, and is provided such that one side of the rectangle of the second Si through-electrode is parallel to the lead wire that passes by two sides of the second Si through-electrode in the rewiring layer.

10. An endoscope comprising:

an insertion portion configured to be inserted into a subject; and the imaging device according to claim 1 provided at a distal end side of the insertion portion.

11. An endoscope system comprising:

the endoscope according to claim 10; and a processing device configured to convert the digital signal output from the imaging device in the endoscope into an image signal.

* * * * *